(12) United States Patent
Schmidtke et al.

(10) Patent No.: US 7,994,350 B2
(45) Date of Patent: Aug. 9, 2011

(54) PROCESS FOR CONTINUOUSLY PREPARING N-ETHYL-2-PYRROLIDONE (NEP)

(75) Inventors: Helmut Schmidtke, Bensheim (DE); Ralph Versch, Speyer (DE); Silke Simon, Wilmslow (GB); Karl Ott, Plankstadt (DE); Ronald Drews, Birkenau (DE); Stephanie Mollner, Mannheim (DE)

(73) Assignee: BASF SE, Ludwigshafen (DE)

( * ) Notice: Subject to any disclaimer, the term of this patent is extended or adjusted under 35 U.S.C. 154(b) by 277 days.

(21) Appl. No.: 12/299,544

(22) PCT Filed: May 10, 2007

(86) PCT No.: PCT/EP2007/054508
§ 371 (c)(1),
(2), (4) Date: Nov. 4, 2008

(87) PCT Pub. No.: WO2007/131929
PCT Pub. Date: Nov. 22, 2007

(65) Prior Publication Data
US 2009/0187030 A1    Jul. 23, 2009

(30) Foreign Application Priority Data
May 16, 2006 (EP) ..................... 06114031

(51) Int. Cl.
C07D 207/267    (2006.01)

(52) U.S. Cl. ..................................... 549/554

(58) Field of Classification Search .................. 548/554
See application file for complete search history.

(56) References Cited

U.S. PATENT DOCUMENTS

| 3,732,087 A | 5/1973 | Grossman |
| 4,885,371 A | 12/1989 | Tracy et al. |
| 7,164,031 B2 * | 1/2007 | Rudloff et al. ............. 548/552 |
| 7,227,029 B2 * | 6/2007 | Rudloff et al. ............. 548/543 |
| 2005/0010057 A1 | 1/2005 | Rudloff et al. |

FOREIGN PATENT DOCUMENTS

| CN | 1199730 | 11/1998 |
| CN | 1237578 | 12/1999 |
| DE | 175007 | 8/1906 |
| EP | 1 004 577 | 5/2000 |
| EP | 1 201 652 | 5/2002 |
| JP | 47 21420 | 10/1972 |
| JP | 7 4020 585 | 5/1974 |
| JP | 2001 002638 | 1/2001 |
| JP | 2001 354646 | 12/2001 |
| WO | 99 52867 | 10/1999 |
| WO | WO 03022811 A1 * | 3/2003 |
| WO | 03 053924 | 7/2003 |
| WO | 2005 090447 | 9/2005 |
| WO | 2005 121083 | 12/2005 |

* cited by examiner

*Primary Examiner* — Jason M Nolan
(74) *Attorney, Agent, or Firm* — Oblon, Spivak, McClelland, Maier & Neustadt, L.L.P.

(57) ABSTRACT

Process for the continuous preparation of N-ethyl-2-pyrrolidone (NEP) by reacting gamma-butyrolactone (GBL) with monoethylamine (MEA) in the liquid phase, wherein GBL and MEA are used in a molar ratio in the range from 1:1.08 to 1:2 an the reaction is carried out at a temperature in the range from 320 to 420° C. and an absolute pressure in the range from 70 to 120 bar.

18 Claims, No Drawings

PROCESS FOR CONTINUOUSLY PREPARING N-ETHYL-2-PYRROLIDONE (NEP)

The present invention relates to a process for the continuous preparation of N-ethyl-2-pyrrolidone (NEP) by reacting gamma-butyrolactone with monoethylamine in the liquid phase.

Owing to particular advantageous properties, NEP is an important, versatile solvent and reaction medium for the chemical industry.

Owing to, inter alia its favorable toxicological properties, it can advantageously substitute other solvents; cf. WO-A-05/090447 (BASF AG).

JP-B-74 020 585 (Mitsubishi Chem. Ind. Ltd.) describes the preparation of pyrrolidones from GBL and primary alkylamines in the presence of water at from 200 to 300° C.

JP-B-47 021 420 (Mitsubishi Chemical Inds) likewise relates to the preparation of pyrrolidones from GBL and primary alkylamines in the presence of water.

JP-A-2001 002638 (Tonen Kagaku KK) discloses a preparation of pure pyrrolidones by adaptation of the residence time and temperature of the liquid in the lower part of a distillation column.

JP-A-2001 354646 (Mitsubishi Chem. Corp.) describes a pyrrolidone composition prepared from GBL and $NH_3$, a primary amine, secondary amine and/or tertiary amine.

U.S. Pat. No. 4,885,371 (GAF Chemicals Corp.) relates to the preparation of N-alkyllactams from corresponding lactones and an alkylamine in the presence of catalytic amounts of boron hydrides.

EP-A-1 004 577 (Mitsubishi Chem. Corp.) teaches the preparation of N-alkyl-2-pyrrolidones by reacting GBL or 4-hydroxybutyric acid with an alkylamine mixture which has a primary amine content of $\leq 85\%$ by weight.

EP-A-1 201 652 (Dairen Chem. Corp.) describes a process for preparing lactams from lactones in the presence of crystalline aluminosilicate zeolite catalysts and water.

It has been recognized according to the present invention that the prior art suffers from, inter alia, the following disadvantages:

a) low space-time yields of NEP,
b) the use of relatively large amounts of water in the synthesis, which leads, inter alia, to low space-time yields of NEP and high energy costs for the preheating of the starting material and the work-up of the reaction product mixture, and
c) the large molar excess of monoethylamine based on GBL, which results in a high engineering outlay in the work-up of the reaction product mixture and recovery of the unreacted monoethylamine and thus high capital and energy costs.

It is an object of the present invention to overcome one or more disadvantages of the prior art and discover an improved, selective process for preparing NEP in high yields and space-time yields (STYs) and high quality (e.g. purity of >99.5% by weight, APHA color number of $\leq 20$, residual GBL content of <0.05% by weight).

We have found that this object is achieved by a process for the continuous preparation of N-ethyl-2-pyrrolidone (NEP) by reacting gamma-butyrolactone (GBL) with monoethylamine (MEA) in the liquid phase, wherein GBL and MEA are used in a molar ratio in the range from 1:1.08 to 1:2 and the reaction is carried out at a temperature in the range from 320 to 420° C. and an absolute pressure in the range from 70 to 120 bar.

The reaction according to the present invention is preferably carried out at a temperature in the range from 330 to 410° C., in particular a temperature in the range from 340 to 380° C., very particularly preferably at a temperature in the range from 345 to 370° C., e.g. in the range from 350 to 366° C.

The reaction according to the present invention is preferably carried out at an absolute pressure in the range from 70 to 110 bar, in particular an absolute pressure in the range from 80 to 110 bar, very particularly preferably an absolute pressure in the range from 80 to 105 bar, e.g. in the range from 90 to 100 bar.

The molar ratio of the starting materials GBL:monoethylamine in the process of the present invention is preferably 1:(1.01-2.0), further preferably 1:(1.02-1.5), in particular 1:(1.03-1.3), very particularly preferably 1:(1.04-1.2), most preferably 1:(1.04-1.15), e.g. 1:1.14.

The feed mixture preferably comprises less than 40% by weight, e.g. less than 15% by weight, particularly preferably less than 10% by weight, very particularly preferably less than 5% by weight, in particular less than 1% by weight, e.g. from 0 to 0.9% by weight, of water at the reactor inlet. In a particularly preferred embodiment, the feed mixture does not comprise any water.

The process of the present invention can, for example, be carried out as follows:

The reactor employed is preferably an upright, slender high-pressure tube which is equipped, after a heat exchanger with bypass, with a depressurization valve controlled via a pressure regulator. The feed streams are preferably preheated by the output from the reactor, so that the reaction temperatures specified according to the present invention can be set in the reactor by means of the heat evolved in the reaction. The reactor is preferably provided with a plurality of sieve trays to prevent backmixing and to improve the establishment of plug flow (effectively a cascade of stirred vessels). The number of sieve trays can be, for example, from 10 to 40, preferably from 20 to 30.

The MEA is preferably used in aqueous solution, e.g. as a 60-80% strength by weight solution, preferably as a $\leq 40\%$ strength by weight, in particular $\leq 31\%$ strength by weight, very particularly preferably $\leq 28.5\%$ by weight, solution, with the water preferably being separated off, preferably by distillation, before introduction into the reactor.

The MEA is preferably used in a purity (calculated on a water-free basis) of $\geq 90\%$ by weight, in particular $\geq 98\%$ by weight, very particularly preferably $\geq 99.8\%$ by weight.

Liquid monoethylamine, if appropriate mixed with recovered monoethylamine from the work-up (see below), is preferably fed by means of a pump, e.g. a diaphragm pump, preferably via a recuperative heat exchanger W and preferably via a, for example, steam-operated heater to the bottom end of the reactor, preferably tube reactor (preferred upflow mode of operation).

GBL is likewise fed by means of a pump, e.g. a diaphragm pump, preferably via a, for example, steam-operated heater into the bottom end of the reactor, preferably tube reactor, with mixing of the starting materials taking place and the starting materials GBL and monoethylamine being present in the abovementioned inventive molar ratio.

In a particularly preferred embodiment, the liquid monoethylamine and the GBL are fed separately into the tube reactor in the center of the bottom of the reactor via a two-fluid injector. While the GBL is introduced through the central nozzle at a high flow velocity (preferably 4-12 m/s), the liquid monoethylamine flows into the reactor through an annular gap around the outside of this nozzle. The starting materials are introduced as a driving jet into a circulation tube which is located in the inlet region of the reactor, encompasses about one third of the free cross section of the tube reactor and has a length of preferably from 1.5 to 2.0 m. The recirculation of liquid which occurs on the outside of the circulation tube and is maintained by means of the driving jet leads to intensive initial contact of the reactants in the above-described, inventive molar ratio.

Continuous exothermic reaction of the GBL with monoethylamine in the liquid phase to form NEP occurs in the reactor under the abovementioned temperature and pressure conditions.

The reaction is preferably carried out in the absence of a catalyst.

The space velocity through the reactor is preferably in the range from 0.5 to 2 kg of GBL/($I_{reactor}$·h), particularly preferably from 1.0 to 1.5 kg of GBL/($I_{reactor}$·h).

The mean residence times of the reaction mixture in the reactor or, if a plurality of reactors is used (cf. below), in all reactors are, on the basis of the density of GBL and monoethylamine (liquid) at room temperature (20° C.), are preferably from 10 to 60 minutes, preferably from 15 to 30 minutes, depending on the throughput.

The space-time yields of NEP Fn the output from the reactor are preferably $\geq$0.5 kg of NEP/(h·$I_{reactor}$, particularly preferably $\geq$1 kg of NEP/(h·$I_{reactor}$) more particularly preferably from 1 to 3 kg of NEP/(h·$I_{reactor}$), very particularly preferably from 1.1 to 2.5 kg of NEP/(h·$I_{reactor}$), e.g. 2 kg of NEP/(h·$I_{reactor}$).

($I_{reactor}$=reactor volume in liters; in the case of a plurality of reactors, total reactor volume in liters).

The reaction product obtained is preferably continuously depressurized from the reactor as feed to a distillation column K1, with all or part of the output from the reactor preferably firstly being passed through the recuperative heat exchanger W (see above) to heat the ethylamine and being cooled in the process.

Overhead distillate from the distillation column K2 (main constituent: NEP, see below) can be mixed beforehand into the feed to the column K1 to recover the NEPs obtained in the overhead distillate from K2.

In the distillation column K1, monoethylamine which is still present and water are distilled off, e.g. at from 40 to 240° C. and from 1 to 2 bar. Energy can be supplied by means of a circulation vaporizer. The distillate is a preferably 15-30% strength by weight, in particular 15-25% strength by weight, e.g. about 20% strength by weight, aqueous monoethylamine solution. Anhydrous monoethylamine can be recovered from the solution by known methods.

The distillation of the monoethylamine still present and the water in this distillation step is preferably carried out in the presence of from 0.05 to 1% by weight, in particular from 0.05 to 0.2% by weight, very particularly preferably from 0.08 to 0.15% by weight, (in each case based on the amount of NEP in the feed to this distillation column) of hydroxides of the metals Na, K, Li, Ba or Ca.

The distillation of the MEA/water mixture in this distillation step is particularly preferably carried out in the presence of NaOH, which is metered as aqueous sodium hydroxide solution into the feed to the column K1 by means of a pump. For example, aqueous 25% strength sodium hydroxide solution is used in such an amount that the concentration of NaOH is from 0.05 to 0.2% by weight, in particular from 0.08 to 0.15% by weight (in each case based on the amount of NEP in the feed to this distillation step).

It has been recognized according to the present invention that this particular way of carrying out the process results in acidic components present in the reaction product (which could cause corrosion problems in the apparatuses) and any residual traces of unreacted GBL being bound (reaction of the GBL to form the corresponding metal salt of gamma-hydroxybutyric acid), so that a particularly pure NEP is finally obtained.

In a preferred procedure the bottoms are subsequently taken from the column K1, cooled if appropriate and conveyed by means of a pump to the column K2 for final distillation of the NEP. Pure NEP is isolated as a liquid stream at a side offtake of the column K2. The temperatures at the bottom are generally from 100 to 140° C. at from 0.01 to 0.02 bar. (Boiling point of NEP: 212° C./1.013 bar). Here too, heat can be supplied by means of a circulation vaporizer. The overhead distillate which also comprises NEP together with MEA and water can be recirculated to the column K1 (see above) and/or to the reactor inlet.

The overhead distillate from the column K1 is preferably passed to a column K3 in which the monoethylamine comprised in the distillate is recovered for reuse in the synthesis.

The monoethylamine solution is also preferably dewatered in the column K3, after which the MEA obtained is fed to the process as fresh starting material.

The process of the present invention gives NEP in yields of >96%, in particular $\geq$97.5%, very particularly $\geq$98%, after distillation.

The conversion of GBL is preferably >99%, in particular $\geq$99.5%, very particularly preferably $\geq$99.9%.

The selectivity (based on GBL) is preferably >96%, e.g. >97%, in particular $\geq$98%, very particularly preferably $\geq$99%.

The NEP obtained according to the present invention has a high quality after distillation:

The purity is preferably >99% by weight, in particular $\geq$99.5% by weight, very particularly preferably $\geq$99.8% by weight.

The GBL content is preferably $\leq$0.05% by weight, in particular $\leq$0.02% by weight, e.g. from 0 to 0.01% by weight, and the monoethylamine content is preferably $\leq$1000 ppm, more preferably $\leq$800 ppm, particularly preferably $\leq$100 ppm, more particularly preferably $\leq$50 ppm, in particular $\leq$20 ppm, e.g. from 0 to 15 ppm; (ppm values are in each case by weight).

The APHA color number in accordance with DIN ISO 6271 of the NEP obtained according to the present invention is preferably $\leq$20, in particular $\leq$10 and is, for example, in particular in the range of from 2 to 8.

The process of the present invention can also be carried out in an apparatus (tube reactor) as described in DE-A-17 95 007, which is hereby expressly incorporated by reference.

The process of the present invention is preferably carried out in a single stage, i.e. in a reactor which may, for engineering reasons, be divided into two or more apparatuses (reactors), with the pressure and temperature conditions specified according to the present invention then prevailing in each of these reactors.

In an alternative embodiment of the process of the present invention, a plurality of reactors, in particular tube reactors, (e.g. two or three reactors, each as described above) operated in the upflow mode can be connected in series, with the pressure and temperature conditions specified according to the present invention prevailing in at least one of these reactors, preferably in the last of these reactors.

An example of such a series arrangement of a plurality of reactors is given in WO-A-99/52867 (cf. the process flow diagram, reactors No. 5, 9 and 13, and the description in that document), which is hereby expressly incorporated by reference.

EXAMPLES

The synthesis of NEP was carried out continuously under the conditions indicated below in a production plant which corresponded largely to the process concept described above, i.e. the starting materials GBL and MEA were preheated in a recuperative heat exchanger and two steam-heated heat exchangers and fed to the synthesis. In one of the columns following the synthesis, the excess ethylamine and the water introduced into the process were separated off and discharged from the process. In a second column, the removal of the residue and the pure distillation of the product were carried out. Work-up and reuse of the ethylamine separated off in the first column were dispensed with.

The reactor was operated in a single pass in the upflow mode. The starting materials monoethylamine (MEA) and GBL were preheated and conveyed by means of pumps to the reactor inlet where the two streams were mixed. The total water content of the starting materials was 14% by weight.

The reaction was carried out under the following conditions during the production experiment:

| Experiment No. 1 | |
| --- | --- |
| Temperature: | 347-355° C. |
| Pressure: | 90 bar |
| Space velocity: | 0.6 kg of GBL/($l_{reactor}$ · h) |
| Molar ratio of MEA:GBL | 1.04 |
| Experiment No. 2 | |
| Temperature: | 353-366° C. |
| Pressure: | 96 bar |
| Space velocity: | 1.2 kg of GBL/($l_{reactor}$ · h) |
| Molar ratio of MEA:GBL | 1.14 |

Space velocity through the reactor in kg of GBL per liter of reactor volume and hour.

The composition of the product stream obtained in the production plant is shown in the following table.

TABLE

| | GC analysis | | | |
| --- | --- | --- | --- | --- |
| Experiment No. | NEP [GC-% by area] | GBL [GC-% by area] | M-NEP*) [GC-% by area] | Others [GC-% by area] |
| 1 | 99.85 | 0.038 | 0.10 | 0.01 |
| 2 | 99.82 | 0.034 | 0.11 | 0.03 |

GC conditions: 30 m DB-1, temperature program: 80° C. inlet temperature, 4° C./min. heating rate, 250° C. final temperature. The residual H$_2$O content is disregarded.
*)M-NEP = methyl-N-ethyl-2-pyrrolidone The NEP yield in the crude output based on the GBL used was >99%.

The space-time yield of NEP in the crude output from the reactor was 0.64 kg of NEP/(h·$l_{reactor}$) (experiment 1) or 1.35 kg of NEP/(h·$l_{reactor}$) (experiment 2).

We claim:

1. A process for the continuous preparation of N-ethyl-2-pyrrolidone (NEP) comprising:
   reacting gamma-butyrolactone (GBL) with monoethylamine (MEA) in the liquid phase at a temperature from 320 to 420° C. and an absolute pressure from 70 to 120 bar with a molar ratio of the starting materials GBL:MEA being in the range from 1:1.08 to 1:2 wherein a feed mixture at a reactor inlet comprising less than 15% by weight of water;
   introducing a reaction product obtained as feed into a column K1 in which MEA and water are distilled off from NEP,
   feeding an overhead distillate from the column K1 to a further column K3 in which dewatering of MEA takes place, with the dewatering of said aqueous MEA solution occurring in the column K3 and the resulting MEA then going as starting material into the process,
   wherein said starting material MEA is introduced into the process as an aqueous MEA solution in column K3.

2. The process according to claim 1, wherein the reaction is carried out at a temperature in the range from 340 to 410° C.

3. The process according to claim 1, wherein the reaction is carried out at an absolute pressure in the range from 80 to 110 bar.

4. The process according to claim 1, wherein GBL and MEA are used in a molar ratio in the range from 1:1.08 to 1:1.5.

5. The process according to claim 1, wherein the reaction is carried out in a single stage.

6. The process according to claim 1, wherein the reaction is carried out in an upright tube reactor.

7. The process according to claim 1, wherein the reaction is carried out in the upflow mode.

8. The process according to claim 7, wherein the monoethylamine and the GBL are fed separately into the tube reactor at the bottom of the reactor via a two-fluid injector.

9. The process according to claim 1, wherein the reaction is carried out in the absence of a catalyst.

10. The process according to claim 1, wherein the MEA is used in a purity (calculated on a water-free basis) of ≧90% by weight.

11. The process according to claim 1, wherein firstly water and monoethylamine (MEA) and finally the N-ethyl-2-pyrrolidone are distilled off from the reaction product after the reaction.

12. The process according to claim 1, wherein the water and monoethylamine are distilled off from the reaction product in the presence of hydroxides of the metals Na, K, Li, Ba or Ca, after the reaction.

13. The process according to claim 1, wherein the N-ethyl-2-pyrrolidone is isolated as a liquid stream from a side offtake of a distillation column.

14. The process according to claim 1 for preparing N-ethyl-2-pyrrolidone with a selectivity of >97%.

15. The process according to claim 1 for preparing N-ethyl-2-pyrrolidone with a selectivity of ≧99.5%.

16. The process according to claim 1 for preparing N-ethyl-2-pyrrolidone having an APHa color number of ≦20.

17. The process according to claim 1 for preparing N-ethyl-2-pyrrolidone in a space-time yield of ≧1 kg NEP/(h·$l_{reactor}$).

18. The process according to claim 1, wherein the water and monoethylamine are distilled off from the reaction product in the presence of NaOH, after the reaction.

* * * * *